United States Patent [19]
Bosslet et al.

[11] Patent Number: 5,877,158
[45] Date of Patent: *Mar. 2, 1999

[54] PRO-PRODRUGS, THEIR PRODUCTION AND USE

[75] Inventors: Klaus Bosslet; Jörg Czech, both of Marburg; Dieter Hoffmann, Marburg-Elnhausen, all of Germany; François Tillequin, Paris, France; Jean-Claude Florent, Les Ulis, France; Michel Azoulay, Paris, France; Claude Monneret, Paris, France; Jean-Claude Jacquesy, Buxerolles, France; Jean-Pierre Gesson, Chansseneuil du Poitou, France; Michel Koch, La Celle Saint Cloud, France

[73] Assignees: Behringwerke Aktiengesellschaft, Marburg, Germany; Laboratoires Hoechst S/A, Paris La Défense, France

[*] Notice: This patent issued on a continued prosecution application filed under 37 CFR 1.53(d), and is subject to the twenty year patent term provisions of 35 U.S.C. 154(a)(2).

[21] Appl. No.: 309,035

[22] Filed: Sep. 20, 1994

[30] Foreign Application Priority Data

Sep. 22, 1993 [EP] European Pat. Off. .............. 93115234

[51] Int. Cl.⁶ .................................................. A61K 47/48
[52] U.S. Cl. ............................ 514/34; 536/6.4; 536/18.7; 552/201
[58] Field of Search ................................ 514/34; 435/78, 435/886; 536/6.4, 18.7; 552/201

[56] References Cited

U.S. PATENT DOCUMENTS 3,803,124  4/1974  Arcamone et al. .
4,337,760  7/1982  Rubin ........................................ 604/52
4,351,937  9/1982  Stefanska et al. ....................... 536/6.4
4,975,278 12/1990  Senter et al. ......................... 424/178.1
5,087,616  2/1992  Myers et al. .............................. 514/21
5,132,290  7/1992  Priebe et al. ............................. 514/34
5,417,970  5/1995  Roskam et al. ........................ 424/85.2
5,470,843 11/1995  Stahl et al. ............................... 514/61
5,561,119 10/1996  Jacquesy et al. ......................... 514/34
5,618,528  4/1997  Cooper et al. ......................... 424/78.3

FOREIGN PATENT DOCUMENTS

P1917874 11/1969 Germany .
  2943438  5/1980 Germany .
  2033393  5/1980 United Kingdom .
WO92/19639 11/1992 WIPO .

OTHER PUBLICATIONS

M. Israel et al., Adriamycin Analogues. J. Med. Chem., 1986, 29, 1273–1276.

Budman et al., Abstract No. 692, presented at the 18th Int. Congress of Chemotherapy, Jun. 27–Jul. 2, 1993.

Ruth Duncan "Review Paper: Drug–polymer conjugates: potential for improved chemotherapy," Anti–Cancer Drugs 1992, vol. 3, pp. 175–210.

Kato et al, A Novel Method of Conjugation of Daunomycin with Antibody with a Poly–L–Glutamic Acid Derivative as Intermediate Drug Carrier, J. Med. Chem., 1984, 27, pp. 1602–1607.

Bundgaerd "The Double Prodrug Concept and its Applications", Advanced Drug Delivery Reviews, 3, pp. 39–65, 1989.

*Primary Examiner*—Robert M. Harrison
*Attorney, Agent, or Firm*—Finnegan, Henderson, Farabow, Garrett & Dunner, L.L.P.

[57] ABSTRACT

Substrate-spacer-prodrug compounds (pro-prodrugs) suited for site specific delivery of drugs, a process of preparing them and their use are described.

14 Claims, No Drawings

PRO-PRODRUGS, THEIR PRODUCTION AND USE

The invention refers to the field of substrate-spacer-prodrug compounds (pro-prodrugs) suited for site specific delivery of drugs, a process of preparing them and their use.

A prodrug may be defined as a chemical which is non-toxic and pharmacodynamically inert, but which can be transformed in vivo to a pharmacologically active drug.

Prodrug transformation can be obtained in vivo using site specifically located enzymes (WO 92/19639), systemically available enzymes (Etoposide phosphate, Ref.: 10th International Congress of Chemotherapy, Jun. 27–Jul. 2, 1993, Abstract Nr. 692), endogenous intracelluar lysosomal proteolytic enzymes (Duncan R., Anti-Cancer Drugs 3, 175–210, 1992) or sequential action of two endogenous "tumor site specific" enzymes (WO 93/08688). This enzyme mediated transformation is most effective with respect to pharmacological efficacy, —if the prodrug is highly detoxified compared to the drug—, can be selectively activated at the target site, and has an extended plasma half-life. Detoxification is optimally obtained, if the hydrophilicity of the prodrug is significantly higher than that of the drug combined with a suitable plasma stability of the prodrug. Prodrug transformation is optimally obtained, if the prodrug can be target site specifically cleaved with high activation rate (Vmax/Km). In addition, plasma half life of prodrugs can be extended by linking to hydrophilic high molecular weight copolymers (Duncan, R., Anti-Cancer Drugs 3, 175–210, 1992).

The prodrugs reported in the literature do not fulfill the criteria for optimal site specific prodrug activation.

Now, new pro-prodrugs with exceptional pharmacological efficacy could be synthesized harbouring all the favourable parameters mentioned above. These pro-prodrugs need activation by at least two different enzymes, one of them located accessible only at the target site, the other one located systemically or in a different compartement/site.

One of the enzymes can be an endogenous enzyme located in the plasma (i.e. esterases, preferentially phosphatases, etc.), the second enzyme could be an endogenous intracellular, preferentially a lysosomal enzyme (i.e. proteases, glycosidases, preferentially glucuronidases, etc.) accessible only at the target site or a targeted enzyme. Targeting preferentially can be obtained using an appropriate fusion protein (EP-A 0501215) or an antibody-enzyme conjugate (WO 88/07378).

Furthermore, pro-prodrug activation can be performed by independent or sequential action of the two enzymes. Independent action means that the pro-prodrugs are substrates for both enzymes; sequential action means that the pro-prodrugs are only substrates for one enzyme and after conversion to prodrugs are substrates for the second enzyme. An independent action of both enzymes is preferable for the efficient release of the drug at the target site. Especially, the combined activity of locally accessible endogenous lysosomal or targeted glycosidases and systemically available esterases/phosphatases results in very efficient target site specific activation.

The pro-prodrugs according to the invention consist of the following common building blocks:

$$(\text{prodrug})_x\text{-S} \qquad \qquad \text{I}$$

wherein S means a substrate moiety to which one or more (x=1 or an integer) prodrug moieties can be bound and wherein the prodrug-S bond or bonds can be cleaved by one enzyme and where for optimal cleavage S can be linked to the prodrug moiety by a spacer which can be self-immolative, whereby a self-immolative spacer is defined as a moiety which is bound through two bonds to two molecules and which eliminates itself from the second molecule if the bond to the first molecule is cleaved and wherein prodrug means a moiety which can be cleaved by another enzyme to generate a pharmacologically active substance and wherein the activating enzymes are at least two different human enzymes one of these located accessible only at the target site of the body.

Preferred S moieties are hydrophilic moieties such as mono- or oligo-phosphate, sulfate, dicarboxylate or polymeric moieties such as polyglutamate, polysialic acid, polyethylen glycol or N-(2-hydroxypropyl)methacrylamide copolymers and preferred prodrugs are compounds of formula II:

$$\text{glycosyl-spacer-drug} \qquad \qquad \text{II}$$

wherein
glycosyl means a mono-, oligo- or polysaccharid or derivative thereof spacer means a moiety as described above and drug means a pharmacologically active substance.

Especially preferred are compounds according to formula III

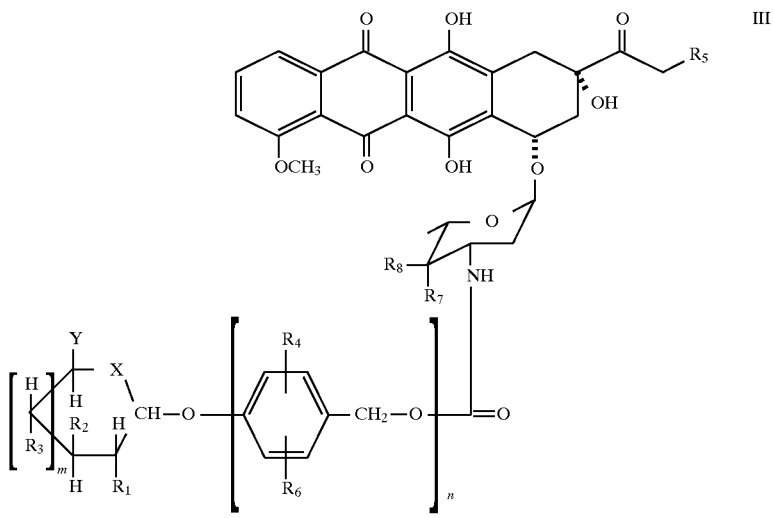

wherein one of $R_{1,2,3,4,5,7,8}$ may be mono- or oligophosphate, sulfate, an acyl moiety such as —OCO(CH$_2$)$_o$—COOH where o is 0 to 100, preferentially 0 to 30, a polymeric residue

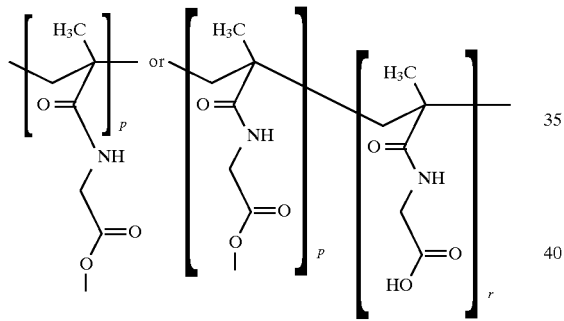

where p and r are 0 to 100, preferentially 1 to 30, a polyglutamat where p is 0 to 100, preferentially 1 to 30, a phosphodiester

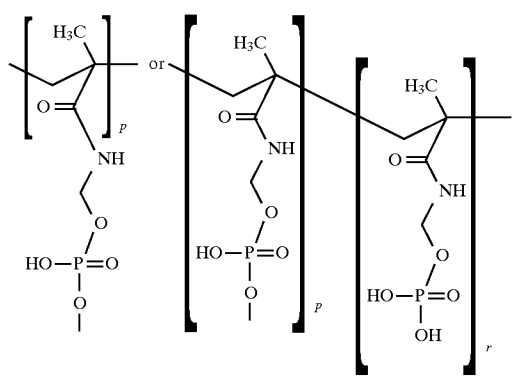

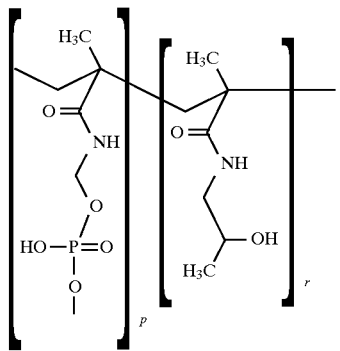

where p and r are 0 to 100, preferentially 1–30
or a phosphodiester substituted with polyethylene glycol or with polysialic acid
and the other R's are independently of each other H or OH,
wherein $R_6$ may be an electron withdrawing residue, preferentially a nitro-, fluoro- or chloro-residue,
wherein n is 0 or 1,
wherein X is O, NH or S,
wherein Y may be COOH, PO$_3$H$_2$, —CH$_2$—COOH, —CH$_2$—PO$_3$H$_2$, CHOH—COOH or CHOH—PO$_3$H$_2$,
wherein m is 0 or 1.

Preferred are compounds, which need activation by at least two different enzymes, one of them located accessible only at the target site, the other one located systemically or in a different compartment/site, compounds, wherein the activating enzymes are hydrolases, e.g. esterases, preferentially phosphatases, combined with glycosidases, preferentially β-glucuronidases.

Enzyme in this application may also mean catalytic antibody.

Preferred embodiments of the invention are depicted in the following. If not described, the compounds can be prepared by prior art methods, for example by activation of the 14-C position of N-[3-nitro-4-(methyl (β-D-glucopyranosyl) uronat)-benzyloxycarbonyl] daunorubicin (described as compound 64b in WO 92/19639) by halogenation according to F. Arcamone (German Patent P 1917874) and further reaction of this intermediate with the desired ligand for example a mono- or dibasic carboxylic acid as described by M. Israel (J. Med. Chem., 1986, 29, 1273–1276). Hydrolysis of the methyl (β-D-glucopyranosyl) uronat moiety to yield the free glucopyranosyluronat can be done according to WO 92/19639 either before or after coupling of the desired ligand.

14-O-Sulfate can be prepared analogously to the phosphate.

Derivatives of N-(4-β-glucuronyl-3-nitrobenzyloxycarbonyl)-doxorubicin-14-O-phosphate, substituted at the phosphate moiety, can be obtained according to J.-B. Ducep (German Patent P 2943438) by reaction of a N-[3-nitro-4-(methyl (β-D-glucopyranosyl) uronat)-benzyloxycarbonyl] daunorubicin-14-halide with the corresponding substituted phosphate. Substances modified at the glucuronic acid or the sugar moiety of the anthracyclin can be obtained by the synthesis according to WO 92/19639, starting with the desired modified glucuronic acid moiety or the sugar modified anthracycline with appropriate blocking groups if necessary.

The citations on this page are herewith incorporated by reference.

Example 1

N-(4-β-glucuronyl-3-nitrobenzyloxycarbonyl)-doxorubicin-14-O-phosphate

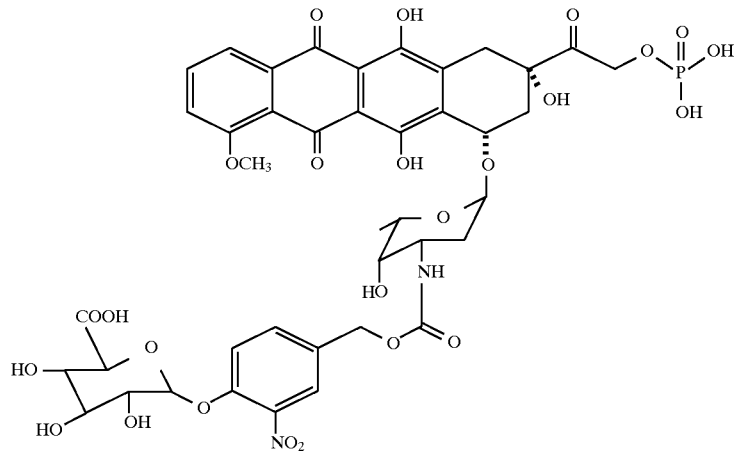

To a solution of N-[3-nitro-4-(methyl (β-D-glucopyranosyl) uronat)-benzyloxycarbonyl] doxorubicin (described as compound 70b in WO 92/19639) (100 mg, 0.11 mmol) in dry acetonitrile (5 ml) was added 1.1 eq. of phosphoryl chlorid (10 μl in 1 ml of acetonitril), in presence of 4 eq. of N,N'-diisopropylethylamine (76 μl in 1 ml of MeCN). The reaction mixture was stirred overnight, and then evaporated (T<40° C.) under reduced pressure to give a syrup. The later was dissolved in a mixture of THF (5 ml) and H$_2$O (3 ml) and cooled at 0° C. then, a 2N aqueous solution of NaOH was added (6 eq., 0.3 ml) and the reaction mixture stirred for 3 hrs. The mixture was carefully acidified until pH=8 before evaporation to dryness. The crude final product was purified on a C18 silicagel column. The later was washed with H$_2$O and the product was eluted with aq. MeCN.

Example 2
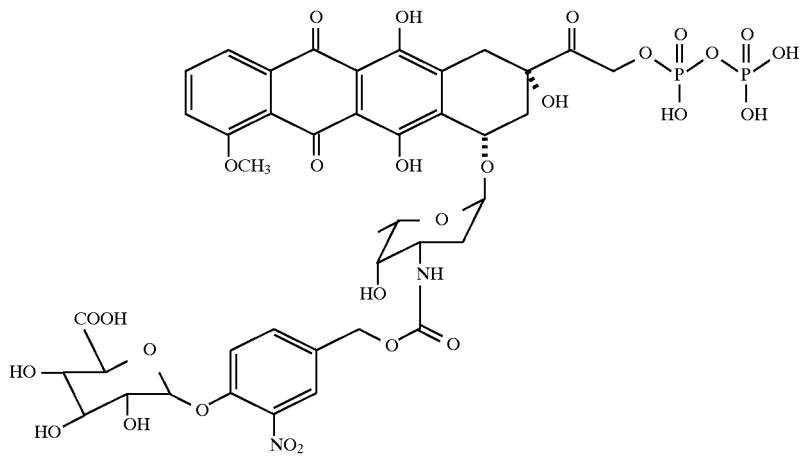
Example 3
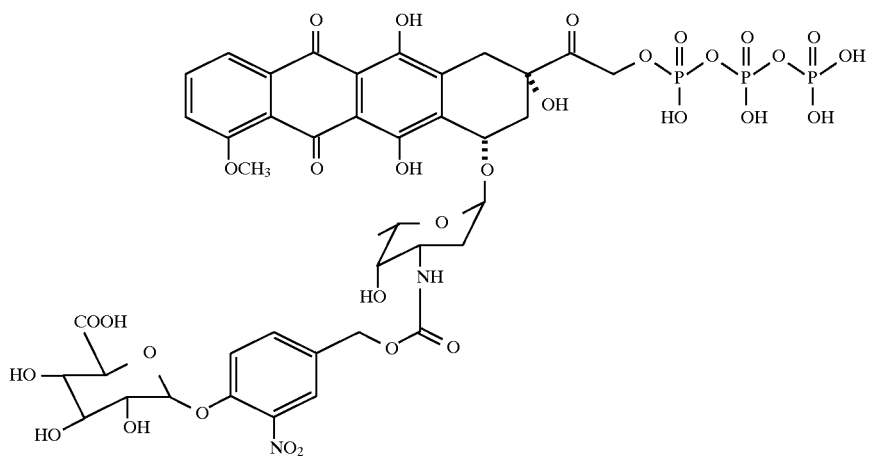
Example 4
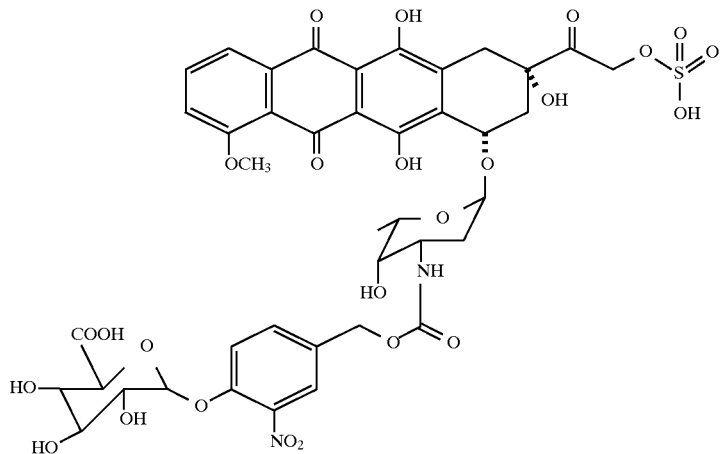

Example 5
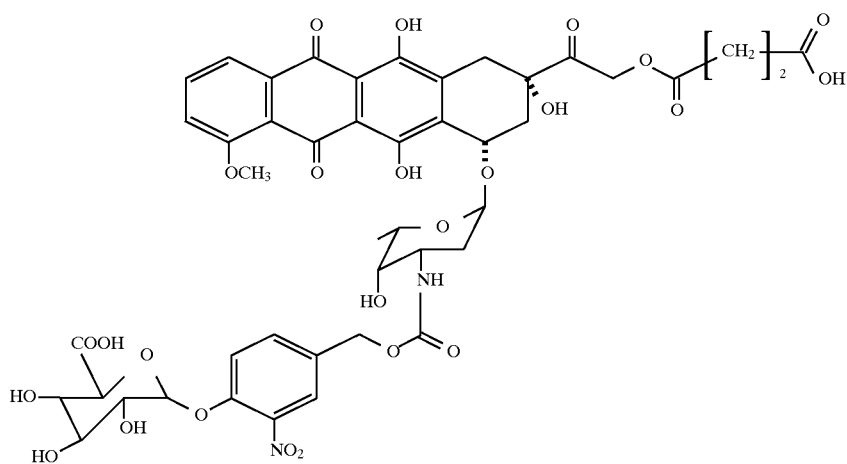
Example 6
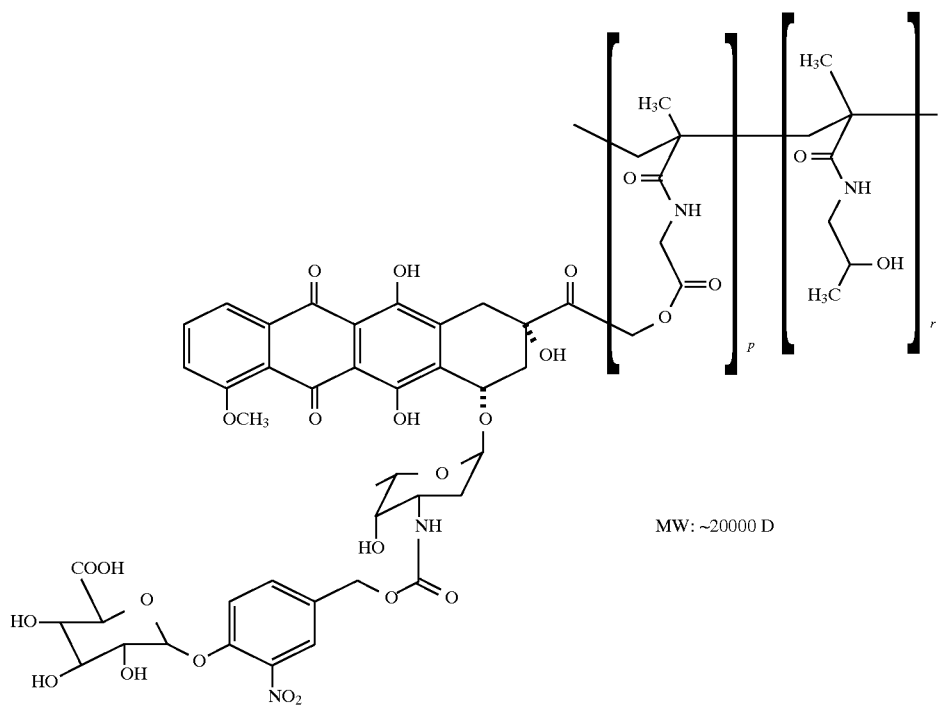
MW: ~20000 D

Example 7
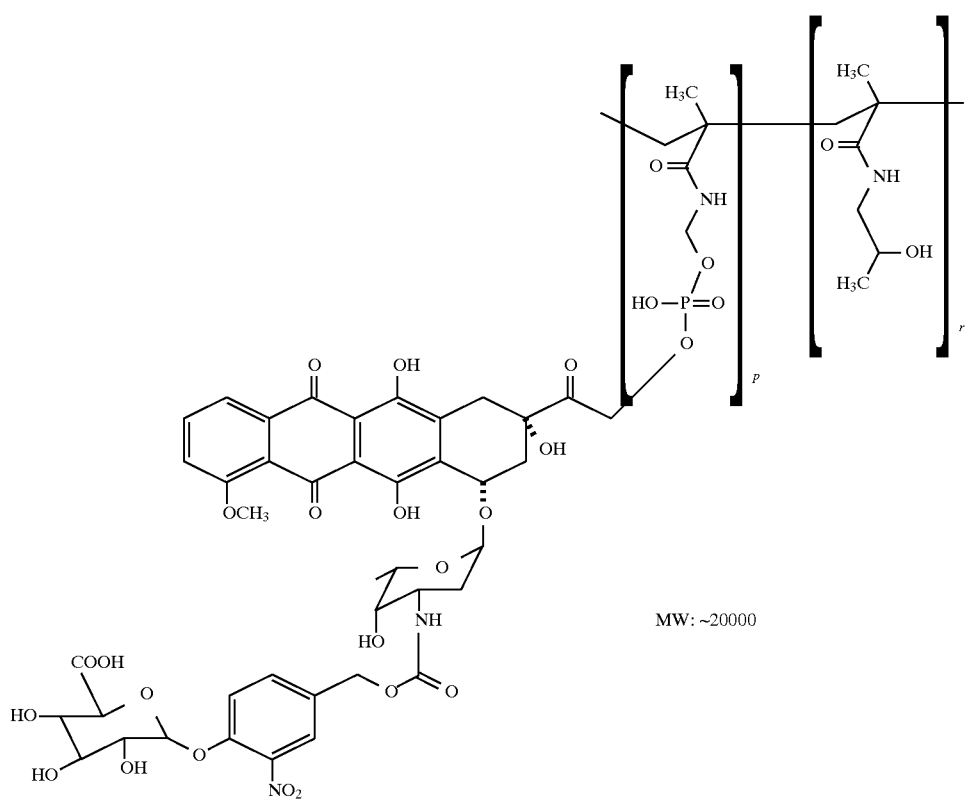
MW: ~20000
Example 8
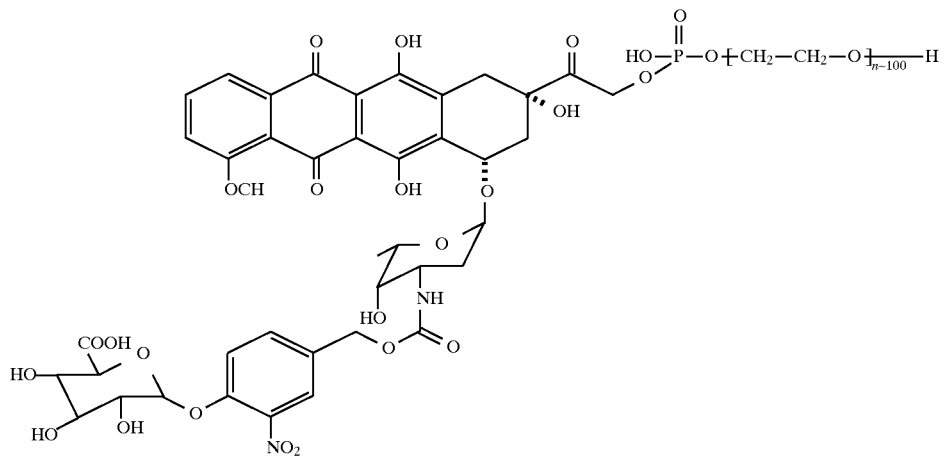

Example 9
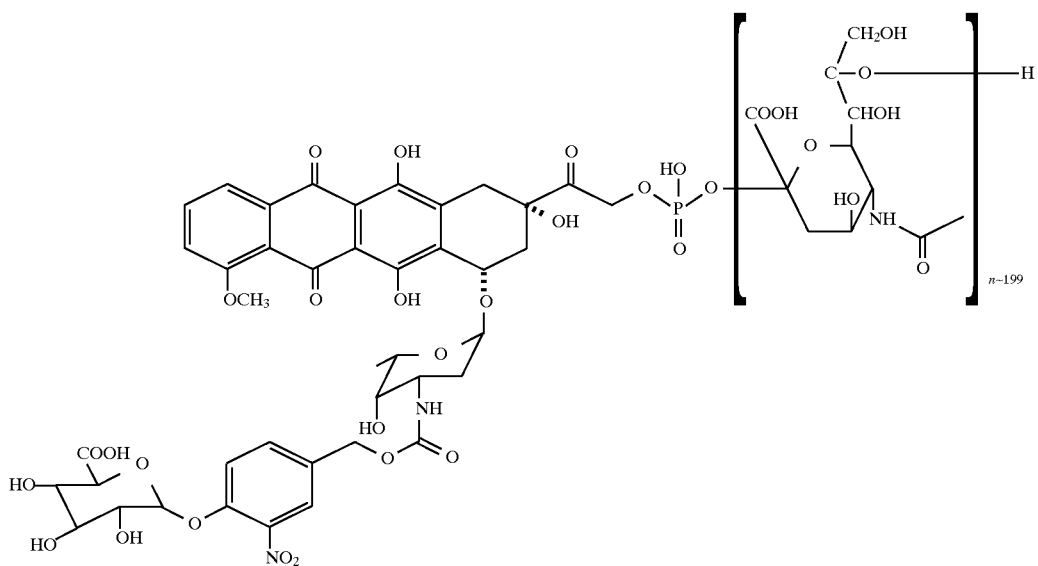
Example 10
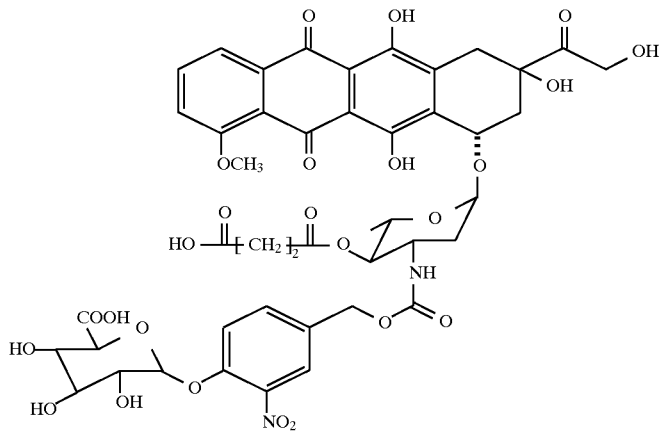
Example 11
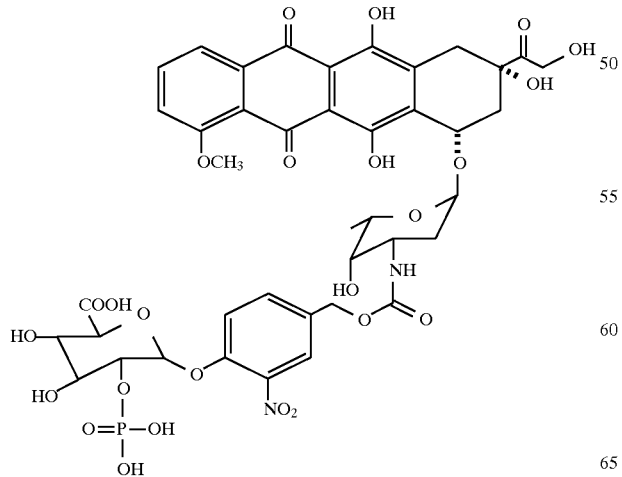

Example 12

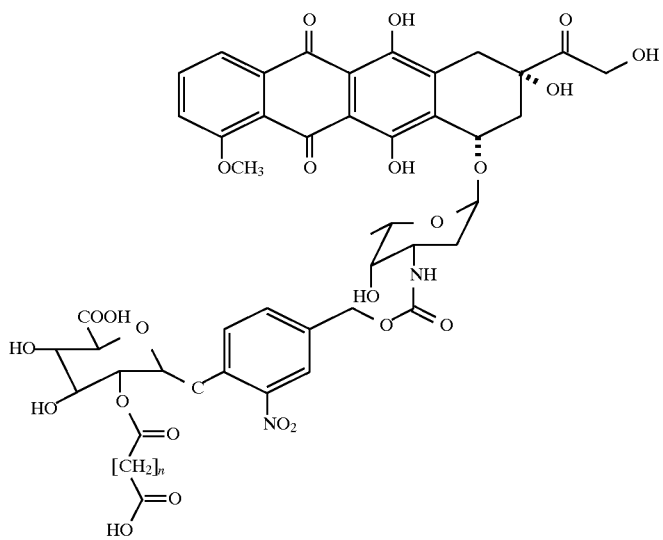

The pro-prodrugs defined in example 1–12 show an increased hydrophilicity compared to the parental prodrug of formula IV

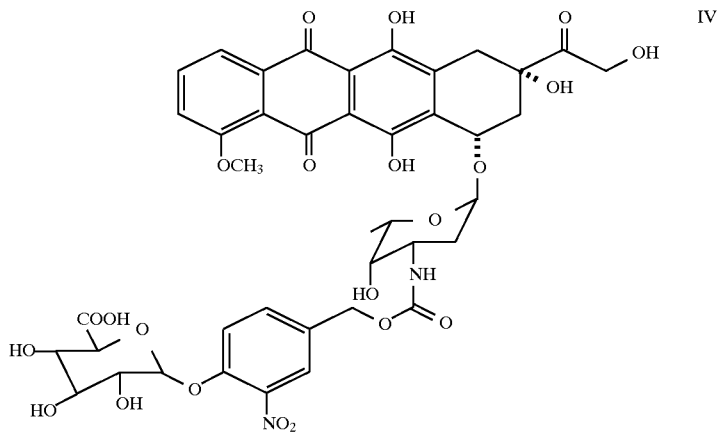

as shown by a reduced octanol water coefficient. This increased hydrophilicity leads to more favourable pharmacokinetics combined with a reduced toxicity and a more efficient site specific activation. This favourable observation is mediated by the action of at least two enzymes. The plasmatic esterases first convert the pro-prodrugs into prodrugs. These prodrugs are site specifically activated to toxic drugs by the action of a targeted glucuronidase and/or by lysosomal glucuronidases liberated in inflamed sites or in necrotic tumor tissues. The above mentioned two step activation mechanism results in a superior drug concentration at the target site compared to the drug concentrations obtained, if the MTD of the drug or the MTD of the parental prodrug is applied. As a consequence therapeutic efficacy is increased.

The use of this new site specific drug delivery systems thus results in a significant increase of the therapeutic window, which is defined as the ratio between the maximally tolerable dose and the minimal effective dose. Further improvements are achievable by encapsulation of these pro-prodrugs in stealth liposomes.

Example 13

Pro-produgs (example 1) can be encapsulated according to D. Papahadjopoulos et al. (PNAS, USA 88:11460–11464, 1991) into stealth liposomes. After i.v. injection into CD1 nu/nu mice the plasma clearance of the pro-prodrug encapsulated into stealth liposomes should be prolonged from ≈20 min for the free pro-prodrug to ≈40 hrs for the encapsulated pro-produg. The significant t½β prolongation should lead to improved pharmacological efficacy.

We claim:

1. A compound of the formula I $$(\text{prodrug})_x\text{-S} \qquad (I)$$

wherein

S is a substrate moiety to which one or more prodrug moieties is or are bound and wherein the prodrug-S bond or bonds can be cleaved by a first activating enzyme and where for optimal cleavage S can be linked to the prodrug moiety by a spacer which can be self-immolative wherein the prodrug is a compound of the formula II glycosyl-spacer-drug (II)

which is cleaved by a second activating enzyme to generate a pharmacologically active substance, and x is 1 or an integer, wherein the first and second activating enzymes are at least two different human enzymes one of them located accessible only at the target site, and the other one located systemically or at a different site of the body, said (prodrug)$_x$-S having the structure:

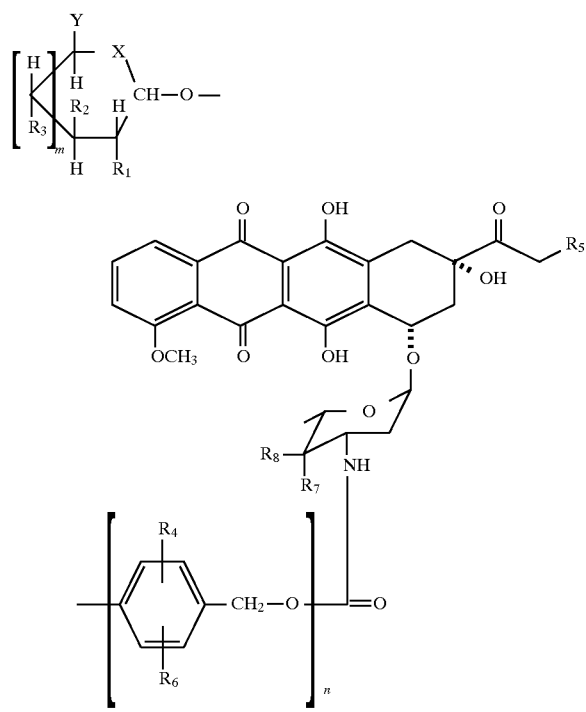

wherein one of R$_{1, 2, 3, 4, 5, 6, 7, 8}$ is a mono- or oligophosphate, sulfate, a polymeric residue

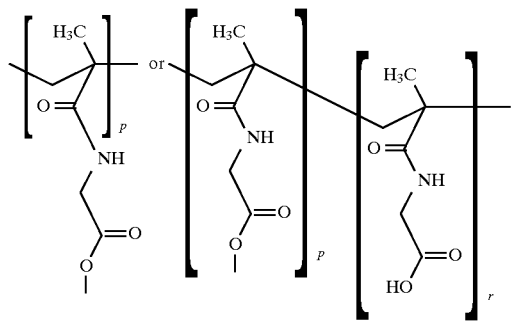

where p and r are 0 to 100,
a polyglutamate where p is 0 to 100,
a phosphodiester

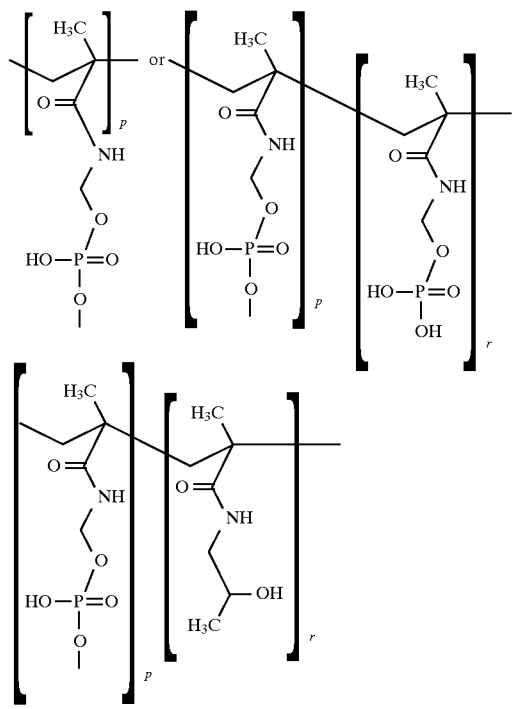

where p and r are 0 to 100,
or a phosphodiester substituted with polyethylene glycol or with polysialic acid
and the other R's are independently of each other H or OH,
wherein R$_6$ may be an electron withdrawing residue,
wherein X is O, NH or S,
wherein Y may be COOH, PO$_3$H$_2$, —CH$_2$—COOH, —CH$_2$—PO$_3$H$_2$, CHOH—COOH or CHOH—PO$_3$H$_2$,
wherein each of m and n is 0 or 1, and one of m or n is 1.

2. A pharmaceutical composition containing an effective amount of a compound of the formula I having the structure set forth in claim 1.

3. A pharmaceutical composition according to claim 2 also containing pretargeted enzymes.

4. A pharmaceutical composition according to claim 2 encapsulated in liposomes.

5. A compound according to claim 1 wherein p and r are 1–30.

6. A compound according to claim 1 wherein in the polyglutamate, p is 1 to 30.

7. A compound according to claim 1 wherein in the phosphodiester p and r are 1–30.

8. A compound according to claim 1 wherein the electron withdrawing residue is a nitro-, fluoro- or chloro-residue.

9. A compound according to claim 1 wherein the first and second activating enzymes are hydrolases.

10. A compound according to claim 9 wherein the firstactivating enzymes are esterases, and the second activating enzymes are glycosidases.

11. A compound according to claim 9 wherein the first activating enzymes are phosphatases.

12. A compound according to claim 10 wherein the glycosidases are β-glucuronidases.

13. A compound according to claim 1, wherein the hydrophilic substrate moiety is a mono- or oligophosphate, sulfate or dicarboxylate.

14. A compound according to claim 1, wherein the polymeric substrate moiety is a polyglutamate, polysialic acid, polyethylene glycol or an N-(2-hydroxypropyl) methacrylamide copolymer.

* * * * *

UNITED STATES PATENT AND TRADEMARK OFFICE
CERTIFICATE OF CORRECTION

PATENT NO.    : 5,877,158  
DATED         : March 2, 1999  
INVENTOR(S)   : Klaus Bosslet et al.

Page 1 of 1

It is certified that error appears in the above-identified patent and that said Letters Patent is hereby corrected as shown below:

<u>Column 17, claim 1,</u>  
Line 52, change "$R_{1,2,3,4,5,6,7,8}$" to -- $R_{1,2,3,4,5,6,7,8}$ --.

Signed and Sealed this

Fourth Day of December, 2001

Attest:

NICHOLAS P. GODICI  
*Attesting Officer*     *Acting Director of the United States Patent and Trademark Office*